US010246511B2

(12) United States Patent
Lee et al.

(10) Patent No.: US 10,246,511 B2
(45) Date of Patent: Apr. 2, 2019

(54) FUSION POLYPEPTIDE CAPABLE OF BINDING SIMULTANEOUSLY TO VEGF-C AND VEGF-D

(71) Applicant: Samsung Electronics Co., Ltd., Suwon-si, Gyeonggi-do (KR)

(72) Inventors: Kwang Hoon Lee, Osan-si (KR); Hyung-Chan Kim, Yongin-si (KR); Sang Yeul Han, Yongin-si (KR); Seok Kyun Kim, Seoul (KR); Kyung Eun Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/667,424

(22) Filed: Aug. 2, 2017

(65) Prior Publication Data

US 2017/0342153 A1 Nov. 30, 2017

Related U.S. Application Data

(62) Division of application No. 14/336,812, filed on Jul. 21, 2014, now Pat. No. 9,725,513.

(30) Foreign Application Priority Data

Jul. 19, 2013 (KR) ........................ 10-2013-0085515

(51) Int. Cl.
*C07K 19/00* (2006.01)
*C07K 14/71* (2006.01)
*A61K 38/18* (2006.01)
*C07K 16/28* (2006.01)

(52) U.S. Cl.
CPC .......... *C07K 16/2863* (2013.01); *C07K 14/71* (2013.01); *C07K 2317/73* (2013.01); *C07K 2317/92* (2013.01); *C07K 2318/20* (2013.01); *C07K 2319/30* (2013.01)

(58) Field of Classification Search
None
See application file for complete search history.

(56) References Cited

U.S. PATENT DOCUMENTS

| 7,399,612 | B2* | 7/2008 | Daly ...................... C07K 14/71 424/134.1 |
| 8,084,234 | B2 | 12/2011 | Papadopoulos et al. |
| 8,703,130 | B2 | 4/2014 | Baehner et al. |
| 2004/0014667 | A1 | 1/2004 | Daly et al. |
| 2006/0110364 | A1 | 5/2006 | Harding |
| 2007/0111281 | A1 | 5/2007 | Sondermann et al. |
| 2008/0242587 | A1 | 10/2008 | Kim et al. |
| 2010/0331250 | A1 | 12/2010 | Zhou et al. |
| 2011/0311546 | A1 | 12/2011 | Oliner et al. |
| 2012/0134993 | A1 | 5/2012 | Pan et al. |
| 2012/0321627 | A1 | 12/2012 | Baehner et al. |
| 2013/0142799 | A1 | 6/2013 | Oliner et al. |

FOREIGN PATENT DOCUMENTS

| CN | 102134277 A | 7/2011 |
| KR | 2008-0032026 A | 4/2008 |
| KR | 2010-0049682 A | 5/2010 |
| KR | 2011-0055726 A | 5/2011 |
| KR | 2011-0134494 A | 12/2011 |

OTHER PUBLICATIONS

Augustin et al., "Control of vascular morphogenesis and homeostasis through the angiopoietin-Tie system," *Nature Reviews Molecular Cell Biology*, 10, pp. 165-177 (2009).
Davis-Smyth, et al., "The second immunoglobulin-lik domain of the VEGF tyrosine kinase receptor Flt-1 determines ligand binding and may initiate a signal transduction cascade," *The EMBO Journal*, vol. 15 No. 18, pp. 4919-4927 (1996).
Ferrara et al., "The biology of VEGF and its receptors," *Nature Medicine*, 9 (6), pp. 669-679 (2003).
Hashizume et al., Complementary Actions of Inhibitors of Angiopoietin-2 and VEGF on Tumor Angiogenesis and Growth, *Cancer Research*, 70(6): 2213-2223 (2010).
Koh et al., Double Antiangiogenic Protein, DAAP, Targeting VEGF-A and Angiopoietins in Tumor Angiogenesis, Metastasis, and Vascular Leakage, *Cancer Cell*, 18: 171-184 (2010).
MacDonald, et al., "Structure of the Extracellular Domain of Tie Receptor Tyrosine Kinases and Localization of the Angiopoietin-binding Epitope," *Journal of Biological Chemistry*, vol. 281, No. 38, pp. 28408-28414 (2006).
Mazzieri et al., Targeting the ANG2/TIE2 Axis Inhibits Tumor Growth and Metastasis by Impairing Angiogenesis and Disabling Rebounds of Proangiogenic Myeloid Cells, *Cancer Cell*, 19: 512-526 (2011).
Stuttfeld, et al. "Structure and Function of VEGF Receptors," *IUBMB Life*, 61(9): pp. 915-922 (2009).
Tammela et al., The biology of vascular endothelial growth factors, *Cardiovascular Research*, 65: 550-563 (2005).
Yang et al., Soluble vascular endothelial growth factor receptor-3 suppresses lymphangiogenesis and lymphatic metastasis in bladder cancer, *Molecular Cancer*, 10(36):1-12 (2011).

* cited by examiner

*Primary Examiner* — Christine J Saoud
*Assistant Examiner* — Jon M Lockard
(74) *Attorney, Agent, or Firm* — Leydig, Voit & Mayer, Ltd.

(57) ABSTRACT

A fusion polypeptide capable of binding simultaneously to angiopoietin 2, VEGF-C and VEGF-D; or capable of binding simultaneously to VEGF-C and VEGF-D, and methods for the preparation and use thereof.

5 Claims, 6 Drawing Sheets
Specification includes a Sequence Listing.

(A)

(B)

FUSION POLYPEPTIDE CAPABLE OF BINDING SIMULTANEOUSLY TO VEGF-C AND VEGF-D

CROSS-REFERENCE TO RELATED APPLICATIONS

This application is a divisional of U.S. patent application Ser. No. 14/336,812 filed on Jul. 21, 2014, and issued as U.S. Pat. No. 9,725,213 on Aug. 8, 2017, which in turn claims the benefit of Korean Patent Application No. 10-2013-0085515 filed on Jul. 19, 2013 with the Korean Intellectual Property Office, the entire disclosure of which is hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: One 48,407 byte ASCII (Text) file named "730335 ST25.TXT revised" created Jul. 13, 2017.

BACKGROUND

1. Field

Provided is a fusion polypeptide capable of binding simultaneously to angiopoietin 2, VEGF-C and VEGF-D, preparation and use thereof. Further, provided is a fusion polypeptide capable of binding simultaneously to VEGF-C and VEGF-D, preparation and use thereof.

2. Description of the Related Art

In a higher organism, blood vessels and lymphatic ducts are formed by vasculogenesis and angiogenesis. Vasculogenesis is a process of forming new blood vessels from hemopoietic precursor cells, which mainly occurs only in very limited situations such as development of embryo and fetus, uterine aging, proliferation of placenta, luteinization and wound healing. To the contrary, angiogenesis is a process of forming new blood vessels through proliferation, migration and differentiation of vascular endothelial cells, and excessive angiogenesis becomes a cause of diseases such as cancers, inflammatory diseases (psoriasis, arthritis, and the like), ophthalmic diseases (diabetic retinopathy), lymphatic proliferative diseases (atherosclerosis, and the like), lymphatic metastasis, and neurodegenerative diseases.

Thus, fundamental treatment of excessive angiogenesis-related diseases may be inhibition of angiogenesis, but currently used angiogenesis inhibitors are generally prepared by an organic synthesis method, cause serious side-effects and the effects are not satisfactory. Particularly, an angiogenesis inhibitor that targets blood vessels supplying nutrients to tumor while not directly acting on cancer cells is considered as one of most promising anticancer therapies because it may avoid drug resistance of cancer cells.

VEGF (Vascular endothelial growth factor) is a representative vascular endothelial growth factor controlling formation and development of blood vessels, and interacts with hematoblast, vascular endothelial precursor cells, and mature endothelial cells. In mammals, VEGF-A, B, C, D and P1GF are known as VEGF. The biological function of VEGF is mediated through VEGF receptors VEGFR1, VEGFR2 and VEGFR3. VEGFR has an extracellular domain consisting of 7 immunoglobulin (Ig)-like domains; a transmembrane domain; and an intracellular domain (a regulatory juxtamembrane domain, an intracellular tyrosine kinase domain, several tyrosine residues). VEGF binds to each specific receptor which is then activated. For example, VEGF-A binds to VEGFR1 and VEGFR2 to perform critical functions for growth, migration and survival of vascular endothelial cells, which are essential for vasculogenesis and angiogenesis. VEGF-B and P1GF bind exclusively to VEGFR1, and studies on the function of VEGF-B in angiogenesis and blood vascular system generation are being continued. To the contrary, VEGF-C and -D bind VEGFR2 and VEGFR3 which is then activated, thereby performing critical functions for growth, migration and survival of lymphatic endothelial cells and formation and maintenenace of lymphatic ducts.

Angiogenesis by VEGF plays important roles in growth, invasion and metastasis of cancers. It was found that VEGF is overexpressed in various tumors such as lung cancer, stomach cancer, renal cancer, bladder cancer, ovarian cancer and uterine cancer, and it was reported that cancer with highly expressed VEGF has a bad prognosis. Thus, studies on inhibition of growth or metastasis of tumors by inhibiting the activity of VEGF or inhibiting the function of cell receptor VEGFR1 or VEGFR2 are being actively progressed. A representative study employs the VEGF trap, which is a water soluble decoy VEGF receptor manufactured by combining domains of VEGFR1 and VEGFR2 on the surface of cells and has high affinity to VEGF-A. Up to date, the antitumor effect of VEGF has been verified, and it has been reported that the VEGF trap has superior antitumor effect compared to VEGF monoclonal antibody bevacizumab or VEGFR2 antibody DC101.

Meanwhile, Angiopoietin-2 (Ang2) is known as a factor relating to cancer angiogenesis and metastasis, as well as ocular diseases involving abnormal vasculogenesis and rheumatoid arthritis. The biological function of angiopoietin-2 is activated by binding to receptor tyrosine kinase (RTK) Tie2. Tie2 has an extracellular domain consisting of Ig-like domain 1, Ig-like domain 2, 3 EGF-like domains, Ig-like domain 3, and 3 fibronectin type-III domains; a transmembrane domain; and an intracellular tyrosine kinase domain. Among the extracellular subdomains of Tie2, Ig-like domain 2 is essential for angiopoietin binding, and Ig-like domains 1 and 3 are required for stable binding of angiopoietin.

The present disclosure inventors further progressed the concept of VEGF trap, to develop fusion polypeptide that binds simultaneously to VEGF-C, VEGF-D and/or angiopoietin 2 to inhibit their intracellular signal transduction, thus having potent effect of inhibiting proliferation and metastasis of cancer cells and lymphangiogenesis,

SUMMARY

Provided is a fusion polypeptide capable of binding simultaneously to angiopoietin 2, VEGF-C and VEGF-D.

Also provided is a fusion polypeptide capable of binding simultaneously to VEGF-C and VEGF-D.

Further provided are nucleic acid molecules encoding the fusion peptide, recombinant vectors including the nucleic acid molecules and cells transformed with the recombinant vector, and related methods of culturing such cells.

It is another embodiment to provide a pharmaceutical composition including the fusion polypeptide.

Yet further provided is a method for treating a neovascular diseases, inhibiting angiogenesis or lymphangiogenesis, or inhibiting proliferation and metastasis of cancer, comprising administering a therapeutically effective amount of the fusion polypeptide to a subject.

DETAILED DESCRIPTION

Figure 1:
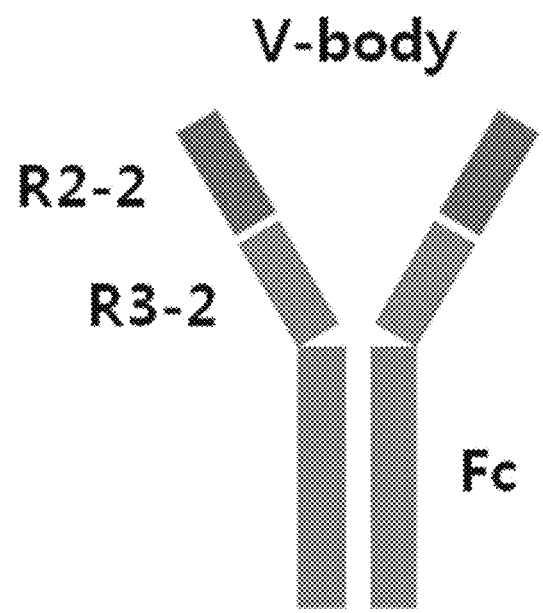
FIG. 1 is a diagram showing a fusion polypeptide (hereinafter, referred to as "V-body") including Ig-like domain 2("R2-2") that is VEGFR2 extracellular domain, Ig-like domain 2("R3-2") that is VEGFR3 extracellular domain, and the Fc region of an immunoglobulin.
Figure 2:
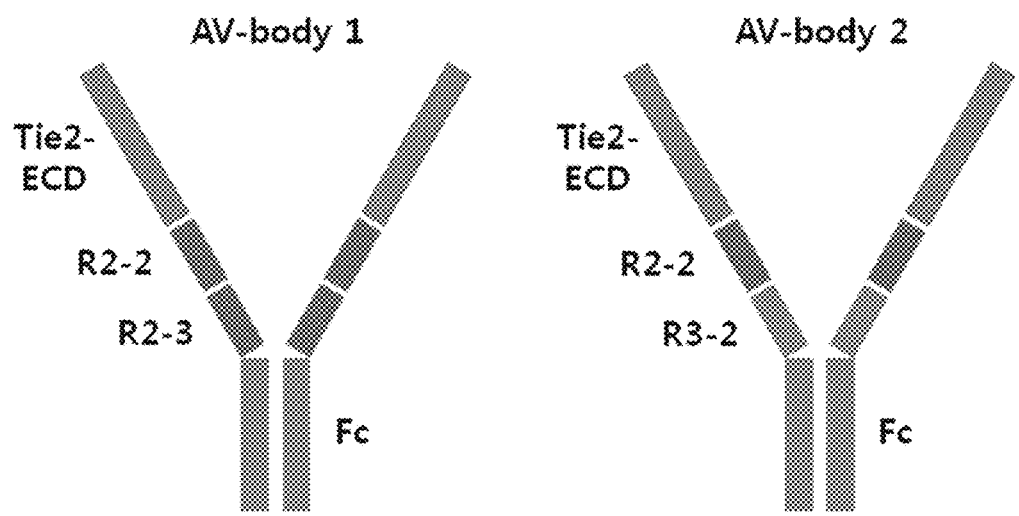
FIG. 2 is a diagram showing two fusion polypeptide called AV-bodies. The left hand fusion polypeptide (hereinafter referred to as "AV-body 1") includes a Tie2 extracellular domain ("Tie2-ECD"), Ig-like domain 2 ("R2-2") and Ig-like domain 3 ("R2-3") that are VEGFR2 extracellular domains, and the Fc region of immunoglobulin. The right side fusion polypeptide (hereinafter, referred to as "AV-body 2") includes Tie2 extracellular domain ("Tie2-ECD"), Ig-like domain 2 ("R2-2") that is VEGFR2 extracellular domain, Ig-like domain 2 ("R3-2") that is VEGFR3 extracellular domain, and the Fc region of an immunoglobulin.

Provided is a fusion polypeptide capable of binding simultaneously to angiopoietin 2, VEGF-C and VEGF-D, comprising
  a Tie2 extracellular domain;
  a VEGFR2 extracellular domain, a VEGFR3 extracellular domain, or both; and
  an Fc region of an immunoglobulin.

Also provided is a fusion polypeptide capable of binding simultaneously to VEGF-C and VEGF-D, including VEGFR2 extracellular domain, VEGFR3 extracellular domain, and the Fc region of immunoglobulin.

In one embodiment, the Tie2 extracellular domain may include Ig-like domain 1, Ig-like domain 2, and 3 EGF-like domains.

In another embodiment, the VEGFR2 extracellular domain may include one or more selected from the group consisting of Ig-like domain 1, Ig-like domain 2, and Ig-like domain 3.

In yet another embodiment, the VEGFR3 extracellular domain may include one or more selected from the group consisting of Ig-like domain 1, Ig-like domain 2, and Ig-like domain 3.

Also provided is a fusion polypeptide including
  a Tie2 extracellular domain comprising Ig-like domain 1, Ig-like domain 2, and three EGF-like domains;
  a VEGFR2 extracellular domain comprising Ig-like domain 2 and Ig-like domain 3; and the Fc region of an immunoglobulin.

Provided is a fusion polypeptide including
  a Tie2 extracellular domain comprising Ig-like domain 1, Ig-like domain 2, and three EGF-like domains;
  a VEGFR2 extracellular domain comprising Ig-like domain 2 and a VEGFR3 extracellular domain comprising Ig-like domain 2; and
  the Fc region of an immunoglobulin.

Further provided is a fusion polypeptide including extracellular domain of Ig-like domain 2, VEGFR3 extracellular domain of Ig-like domain 2, and the Fc region of immunoglobulin.

Also provided is a fusion polypeptide including
  a Tie2 extracellular domain comprising amino acid residues 1st to 345th of SEQ ID NO: 1; and
  a VEGFR2 extracellular domain comprising amino acid residues 123th to 326th of SEQ ID NO: 2; and
  the Fc region of an immunoglobulin.

Also provided is a fusion polypeptide including
  a Tie2 extracellular domain comprising amino acid residues 1st to 345th of SEQ ID NO: 1;
  a VEGFR2 extracellular domain comprising amino acid residues 120th to 220th SEQ ID NO: 2, and a VEGFR3 extracellular domain comprising amino acid residues 136th to 226th of SEQ ID NO: 3; and
  the Fc region of an immunoglobulin.

Also provided is a fusion polypeptide including amino acid sequence of SEQ ID NO: 6 or SEQ ID NO: 7.

Also provided is a fusion polypeptide including a VEGFR2 extracellular domain comprising amino acid residues 120th to 220th of SEQ ID NO: 2, a VEGFR3 extracellular domain comprising amino acid residues 136th to 226th of SEQ ID NO: 3, and the Fc region of an immunoglobulin.

Also provided is a fusion polypeptide including a polypeptide consisting of amino acid sequence of SEQ ID NO: 4, and the Fc region of immunoglobulin.

Also provided is a nucleic acid molecule encoding a fusion polypeptide as described herein.

Also provided is a recombinant vector including the nucleic acid molecule.

Also provided is a cell transformed with the recombinant vector.

Also provided is a method for preparing a fusion polypeptide, including culturing cells transformed with the recombinant vector.

Also provided is a pharmaceutical composition for prevention or treatment of neovascular diseases, including the fusion polypeptide.

In an embodiment, the neovascular disease may include cancer, diabetic retinopathy, retinopathy of prematurity, corneal graft rejection, neovascular glaucoma, erythrosis, proliferative retinopathy, psoriasis, hemophilic arthropathy, capillary proliferation in atherosclerosis plaque, keloid, wound granulation, vascular adhesion, rheumatoid arthritis, osteoarthritis, autoimmune disease, crohn's disease, restenosis, atherosclerosis, intestinal adhesion, cat scratch disease, ulcer, liver cirrhosis, nephritis, diabetic nephropathy, malignant nephrosclerosis, thrombotic microangiopathy, organ transplant rejection, glomerulopathy, diabetes mellitus, inflammation, or neurodegenerative disease.

Also provided is a method for treating neovascular diseases, including administering an effective amount of the fusion polypeptide to a subject.

Also provided is a method for inhibiting angiogenesis and/or lymphovasculogenesis, including administering an effective amount of the fusion polypeptide to a subject.

Also provided is a method for inhibiting proliferation and/or metastasis of cancer, including administering an effective amount of the fusion polypeptide to a subject.

Also provided is a method for simultaneously inhibiting VEGF-C and VEGF-D, including administering an effective amount of the fusion polypeptide to a subject.

Also provided is a method for simultaneously inhibiting angiopoietin 2, VEGF-C and VEGF-D, including administering an effective amount of the fusion polypeptide to a subject.

Also provided is a use of the fusion polypeptide for prevention or treatment of neovascular diseases.

Also provided is a use of the fusion polypeptide in the preparation of medicine for prevention and/or treatment of neovascular diseases.

Hereinafter, the present disclosure will be explained in detail.

As used herein, the term "fusion polypeptide" refers to two or more different polypeptides or proteins artificially connected together. In one embodiment, in order to bind simultaneously to VEGF-C, VEGF-D and/or angiopoietin2 to inhibit signal transduction thereof, the fusion polypeptide may consist of extracellular domain of each receptor VEGFR2, VEGFR3 and/or Tie2. In another embodiment, the fusion polypeptide may include the Fc region of an immunoglobulin to increase in vivo stability.

The fusion polypeptide may act as a chimeric decoy receptor. A decoy receptor is a "fake" receptor that decoys a substrate and binds thereto, and aims to inhibit binding of a substrate to a true receptor. Thus, the fusion polypeptide may consist of minimum binding domains for binding simultaneously to VEGF-C, VEGF-D and/or angiopoietin 2, and inhibits binding of VEGF-C, VEGF-D and/or angiopoietin 2 to each receptor VEGFR2, VEGFR3, and Tie2, thereby acting as a therapeutic agent of neovascular diseases that has potent effects of inhibiting proliferation and metastasis of cancer cells, and lymphangiogenesis.

Tie2 has an extracellular domain comprising Ig-like domain 1, Ig-like domain 2, 3 EGF-like domains, Ig-like domain 3, and 3 fibronectin type-III domains; a transmembrane domain; and an intracellular tyrosine kinase domain (Augustin H G et al., Nature Reviews Molecular Cell Biology, 2009, 10, 165~177). The extracellular domains of Tie2 may be used as a fusion polypeptide component, and preferably, among the extracellular domains of Tie2, minimum extracellular subdomains required for binding to angiopoietin may be selected to constitute fusion polypeptide.

In one embodiment, the Tie2 extracellular domains may include Ig-like domain, Ig-like domain 2 and 3 EGF-like domains. These are believed to be minimum parts found through 3-dimensional structure analysis to independently stably exist while Tie2 binds to anigiopoietin 2. The amino acid sequence of Tie2 is known as GenBank Registration NO: AAH35514.2 (SEQ ID NO: 1), and among them, the fusion polypeptide may include a polypeptide including amino acid residues 1st~345th of SEQ ID NO: 1 (e.g., SEQ ID NO: 5).

VEGFR2 and VEGFR3 have an extracellular domain comprising 7 immunoglobulin (Ig)-like domains; a transmembrane domain; and intracellular domains (a regulatory juxtamembrane domain, am intracellular tyrosine kinase domain, several tyrosine residues). The extracellular domains of VEGFR2 and VEGFR3 may be used as a component of the fusion polypeptide, and preferably, among the extracellular domains of VEGFR2 and VEGFR3, minimum extracellular domains capable of binding to VEGF-C and VEGF-D may be selected to constitute the fusion polypeptide.

In another embodiment, the VEGFR2 extracellular domain may be one or more selected from the group consisting of Ig-lke domain 1, Ig-like domain 2 and Ig-like domain 3, and the VEGFR3 extracellular domain may be one or more selected from the group consisting of Ig-like domain 1, Ig-like domain 2 and Ig-like domain 3 (Ferrara N et al., Nature Medicine, 2003, 9, 669~676).

In another embodiment, the amino acid sequence of VEGFR2 is known as GenBank Registration NO: AAH35514.2 (SEQ ID NO: 2), and among them, the fusion polypeptide may include a polypeptide including amino acid residues 120th~220th of SEQ ID NO: 2, or polypeptide including amino acid residues 123th~326th of SEQ ID NO: 2. The amino acid sequence of VEGFR3 is known as GenBank Registration NO: NP 891555.2 (SEQ ID NO: 3) and among them, the fusion polypeptide may include a polypeptide including amino acid residues 136th~226th of SEQ ID NO: 3.

And, the fusion polypeptide may include the Fc region of immunoglobulin at N-terminal or C-terminal as a component. The Fc region may be of an immunoglobulin class selected from the group consisting of IgA, IgD, IgE, IgG and IgM, and the Fc of IgG may be selected from homogeneous IgG1, IgG2, IgG3, and IgG4, and any allotypes thereof. It may include a whole or a part of CH2 and CH3 constant domains, but not limited thereto.

The Fc region may function as various effectors to remove antigens, and the functions may be largely divided as follows. First, the Fc region of antibody binds to Fc receptor (Fc R) on the surface of effector cell such as macrophage or NK cell to promote phagocytosis or degradation, thereby removing cells containing or bound to antigen (antibody-dependent cell-mediated cytotoxicity (ADCC)). Second, complement cascade is activated by the Fc region of antibody to make a hole in cell membranes, thereby destructing pathogenic cells (complement dependent cytotoxicity (CDC)). In addition to effector functions, another important function of the Fc region is to increase blood residence time of antibody. FcRn (neonatal Fc receptor) existing in vascular endothelial cells may bind between CH2 and CH3 of the Fc region to prevent degradation of IgG thus prolonging blood half life.

In addition to these biological functions, the Fc region may be used as affinity-tag for convenience of purification of fusion polypeptide expressed in culture medium.

According to one embodiment, the fusion polypeptide may include (i) Tie2 exctacellular domains of Ig-like domain 1, Ig-like domain 2 and 3 EGF-like domains; (ii) VEGFR2 extracellular domains of Ig-like domain 2 and Ig-like domain 3; and (iii) the Fc region of immunoglobulin.

According to another embodiment, the fusion polypeptide may include (i) Tie2 extracellular domains of Ig-like domain 1, Ig-like domain 2 and 3 EGF-like domains; (ii) VEGFR2 extracellular domain of Ig-like domain 2, and VEGFR3 extracellular domain of Ig-like domain 2, and (iii) the Fc region of immunoglobulin.

According to yet another embodiment, the fusion polypeptide may include (i) polypeptide including 1st~345th amino acid residues of Tie2; (ii) polypeptide including amino acid residues 123th~326th of VEGFR2; and (iii) the Fc region of immunoglobulin.

According to yet another embodiment, the fusion polypeptide may include (i) polypeptide including 1st~345th amino acid residues of Tie2; (ii) polypeptide including amino acid residues 120th~220th of VEGFR2, and polypeptide including amino acid residues 136th~226th of VEGFR3; and (iii) the Fc region of immunoglobulin.

According to yet another embodiment, the fusion polypeptide may include extracellular domain of Ig-like domain 2, VEGFR3 extracellular domain of Ig-like domain 2, and the Fc region of immunoglobulin.

According to yet another embodiment, the fusion polypeptide may include polypeptide including amino acid residues 120th~220th of VEGFR2, polypeptide including amino acid residues 136th~226th of VEGFR3, and the Fc region of an immunoglobulin.

According to yet another embodiment, the fusion polypeptide may include a polypeptide consisting of amino acid sequence of SEQ ID NO: 4, SEQ ID NO: 6 or SEQ ID NO: 7, and the Fc region of immunoglobulin.

The fusion polypeptide may further include a signal sequence so as to facilitate extracellular secretion when culturing cells. And, each polypeptide constituting the fusion polypeptide may be directly connected each other, or connected through a linker, a spacer or a connector such as a restriction enzyme recognition site. If connected through a linker, it may not preferably decrease whole activity.

As used herein, the term "linker" refers to a peptide inserted between proteins so as to increase structural flexibility of there proteins to enhance the activity of each protein, when connecting extracellular domains of each receptor to prepare fusion polypeptide. The kind of the linker or the number of amino acid is not specifically limited as long as it may minimize immune reactions, but 1 to 20 amino acids are preferable, and 1 to 5 amino acids is more preferable.

The fusion polypeptide may include variants of fusion polypeptide as well as polypeptide having wild type amino acid sequence. The variant of fusion polypeptide refers to protein having different sequence from wild type amino acid sequence by deletion, insertion, non-conservative or conservative substitution of at least one amino acid residue, or combination thereof. Amino acid exchange in protein and peptide that does not generally change the activity of molecules is known in the art (H. Neurath, R. L. Hill, The Proteins, Academic Press, New York, 1979).

And, the fusion polypeptide may be modified by phosphorylation, sulfation, acrylation, glycosylation, methylation, farnesylation, and the like. The variant or modified product is a functional equivalent to natural protein exhibiting identical biological activity, but if necessary, the property of the polypeptide may be varied. In an embodiment, structural stability of protein to heat, pH, and the like may be increased or the activity of protein may be increased by variation and modification of amino acid sequence.

The fusion polypeptide may be chemically synthesized or produced by gene recombination, and it may be produced by transforming host cells using a recombinant vector and separating and purifying expressed protein.

Accordingly, there are provided, for preparation of fusion polypeptide, a nucleic acid molecule coding the fusion polypeptide, a recombinant vector including the same, a cell transformed with the recombinant vector, and a method for preparing fusion polypeptide using the same.

Various vectors such as plasmid, virus, cosmid, and the like may be used as the vector for preparing fusion polypeptide. A recombinant vector includes a cloning vector and an expression vector. A cloning vector includes an origin of replication, for example, an origin of replication of plasmid, phage or cosmid, and it is replicon to which another DNA fragment may be attached to replicate the attached fragment. An expression vector was developed for use in protein synthesis, and those commonly used for expression of foreign protein in plants, animals or microorganisms may be used. The recombinant vector may be constructed by various methods known in the art.

A recombinant vector is a carrier in which foreign DNA fragment is inserted, and generally refers to a fragment of double stranded DNA. The recombinant vector should be operably linked to transcription and translation regulatory sequence so as to increase expression level of transformed gene in host cell. The recombinant vector is a genetic construct including operably linked essential regulatory element so as to express genetic insert in cells of a subject, and standard recombinant DNA technology may be used to prepare the genetic construct.

The kind of the recombinant vector is not specifically limited as long as it may express target gene in various host cells of prokaryotic cells and eukaryotic cells and produce target protein, but a vector that may mass-produce foreign protein of similar forms to natural protein while possessing a promoter exhibiting potent activity and strong expression is preferable. A recombinant vector preferably includes at least, a promoter, an initiation codon, genes coding target protein, a termination codon, and a terminator. Besides, it may appropriately include DNA coding signal peptide, enhancer sequence, 5' and 3' non-translated region of target gene, selection marker region, or replicable unit, and the like.

The host cell that may be transformed with the recombinant vector may include prokaryotic cells and eukaryotic cells, and host with high DNA introduction efficiency and high expression efficiency of the introduced DNA may be commonly used. The prokaryotic cells may include enterobacteria and strains such as *E. coli* JM109, *E. coli* BL21, *E. coli* RR1, *E. coli* LE392, *E. coli* B, *E. coli* X 1776, *E. coli* W3110, strain of the genus *Bacillus* such as *Bacillus subtillis*, *Bacillus thuringiensis*, *Salmonella typhimurium*, *Serratia marcescens*, and various *Pseudomonas* sp., and the eukaryotic cells may include yeast (*Saccharomyce cerevisiae*), insect cells, plant cells and animal cells, for example, CHO cell line (Chinese hamster ovary), W138, BHK, COS-7, 293, HepG2, 3T3, RIN and MDCK cell lines, and the like.

To prepare a transformant by introducing a recombinant vector into host cell, any introduction method widely known in the art may be used. For example, if the host cell is a prokaryotic cell, a CaCl$_2$ method or electroporation, and the like may be used, and if the host cell is eukaryotic cell, microinjection, calcium phosphate precipitation, electroporation, liposome-mediated transfection and gene bombardment, and the like may be used, but not limited thereto.

The selection of transformed host cells may be easily conducted by any methods widely known in the art, using a phenotype expressed by selection marker. For example, if the selection marker is a specific antibiotics resistant gene, a transformant may be easily selected by culturing a transformant in a medium containing the antibiotics.

If transformant expressing the recombinant vector is cultured in a nutrient medium, useful protein may be prepared and separated in a large quantity. The medium and culture conditions may be appropriately selected from those commonly used according to host cell. When culturing, conditions such as temperature, pH of medium and culture time, and the like should be appropriately controlled so as to be suitable for growth and development of cells and mass production of protein.

Fusion polypeptide produced from transformed cell may be recovered directly from medium or as a lysis product of cells. In the case of a membrane-binding type, it may be isolated from a membrane using a suitable surfactant solution (for example, triton-X 100) or by enzymatic cleavage. Cells used for expression of fusion polypeptide may be destructed by various physical or chemical means such a repetition of freeze-thaw, sonication, mechanical destruction or an agent for degrading cells, and may be separated and purified by common biochemical separation method. For example, the separation method includes electrophoresis, centrifugation, precipitation, dialysis, chromatography (ion exchange chromatography, affinity chromatography, immunoaffinity chromatography, reverse phase HPLC, gel permeation HPLC), isoelectric focusing and various modified and combined methods thereof, but not limited thereto.

There is provided a potent therapeutic agent for neovascular diseases that may bind simultaneously to VEGF-C and VEGF-D to inhibit intracellular signal transduction thereof, thereby inhibiting proliferation and metastasis of cancer cells and lymphogenesis, and to achieve this, there is provided a fusion polypeptide with increased in vivo stability by combining extracellular domains of VEGF-C and -D-recognizing receptors VEGFR2 and/or VEGFR3 and fusing Fc thereto. Furthermore, there is provided a fusion polypeptide that also inhibits the function of angiopoietin 2 and thus has more potent effect of inhibiting angiogenesis, by additionally introducing a part of angiopoietin 2 receptor Tie2.

The fusion polypeptide may be a chimeric decoy receptor that may bind simultaneously to VEGF-C, VEGF-D and/or angiopoietin 2, and it may be used for treatment of neovascular diseases caused by angiogenesis of VEGF-C, VEGF-D and/or angiopoietin 2.

Thus, there is provided a pharmaceutical composition for prevention or treatment of neovascular diseases, including the fusion polypeptide.

As used herein, the term "prevention" refers to all acts of inhibiting or delaying occurrence, diffusion or recurrence of cancer or angiogenesis-related diseases by administration of the composition, and "treatment" refers to all acts of improving or favorably modifying symptoms of the diseases by administration of the composition.

As used herein, the term "angiogenesis" refers to a process of newly forming blood vessels, i.e., generating new blood vessels in cells, tissues or organs, "neovascular" refers to newly formed blood vessels through angiogenesis, and "angiogenesis" and "neovascular" may be interchangeably used in the present invention. In the present invention, "neovascualr diseases" or "angiogenesis-related diseases" mean diseases caused by abnormal progression of the angiogenesis.

The angiogenesis-related diseases that can be prevented or treated by the composition may include cancer, inflammatory disease, ophthalmic disease, lymphatic proliferative disease, lymphatic metastasis, neurodegenerative disease. More specifically, it may include cancer, diabetic retinopathy, retinopathy of prematurity, corneal graft rejection, neovascular glaucoma, erythrosis, proliferative retinopathy, psoriasis, hemophilic arthropathy, capillary proliferation in atherosclerosis plaque, keloid, wound granulation, vascular adhesion, rheumatoid arthritis, osteoarthritis, autoimmune disease, crohn's disease, restenosis, atherosclerosis, intestinal adhesion, cat scratch disease, ulcer, liver cirrhosis, nephritis, diabetic nephropathy, malignant nephrosclerosi s, thrombotic microangiopathy, organ transplant rejection, glomerulopathy, diabetes mellitus, inflammation, or neurodegenerative disease.

Cancers that may be prevented or treated by the composition may include uterine cervical cancer, lung cancer, pancreatic cancer, non-small cell lung cancer, liver cancer, colon cancer, bone cancer, skin cancer, head cancer, cerbical cancer, skin melanoma, intraocular melanoma, uterine cancer, ovarian cancer, rectal cancer, liver cancer, cerebral tumor, bladder cancer, blood cancer, gastric cancer, anal cancer, colon cancer, breast cancer, fallopian tube carcinoma, endometrial carcinoma, vaginal cancer, vulvar cancer, Hodgkin's disease, esophageal cancer, small intestine cancer, endocrine adenocarcinoma, thyroid cancer, parathyroid cancer, adrenal gland cancer, soft tissue sarcoma, urethral cancer, penis cancer, prostate cancer, bladder cancer, renal cancer, ureteral cancer, renal cell carcinoma, renal pelvis carcinoma, central nervous system tumor, spinal cord tumor, brain stem glioma, pituitary adenoma, and the like. The pharmaceutical composition may effectively inhibit migration of cancer cells, and thus, it may be useful for prevention and treatment of cancer metastasis.

The pharmaceutical composition, if necessary, may further include pharmaceutically acceptable carriers, diluents and/or excipients in commonly used amounts. The pharmaceutically acceptable carrier may include lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, and mineral oil, and the like, but is not limited thereto. The pharmaceutical composition may further include a lubricant, a wetting agent, a sweetner, a favouring agent, an emulsifier, a suspension, a preservative, and the like, besides the above ingredients.

The composition may be formulated into various forms including oral dosage forms such as powder, granule, tablet, capsule, suspension, emulsion, syrup, aerosol, and the like, injections such as a sterilized solution for injection, and the like, and it may be orally administered or administered via various routes including intravenous, intraperitoneal, subcutaneous, rectal, local administration, and the like.

The composition may further include known anticancer drugs or angiogenesis inhibitors in addition to fusion polypeptide as active ingredients, and may be combined with other therapies known to be used for treatment of these diseases. Other therapies may include chemotherapy, ratiotherapy, hormonal therapy, bone marrow transplantation, stem cell replacement therapy, other biological therapy, immunotherapy, and the like, but are not limited thereto.

Specific examples of the anticancer drugs that may be included in the pharmaceutical composition may include DNA alkylating agents such as mechloethamine, chlorambucil, phenylalanine, mustard, cyclophosphamide, ifosfamide, carmustine (BCNU), lomustine (CCNU), streptozotocin, busulfan, thiotepa, cisplatin and carboplatin; anticancer antibiotics such as dactinomycin (actinomycin D), doxorubicin: adriamycin, daunorubicin, idarubicin, mitoxantrone, plicamycin, mitomycin and C Bleomycin; and plant alkaloids such as vincristine, vinblastine, paclitaxel, docetaxel, etoposide, teniposide, topotecan and iridotecan, and the like, but are not limited thereto.

Specific examples of the angiogenesis inhibitors that may be included in the pharmaceutical composition may include angiostatin (plasminogen fragment); anti-angiogenic antithrombin III; angiozyme; ABT-627; Bay 12-9566; benefin; bevacizumab; BMS-275291; cartilage-derived inhibitor, (CDI); CAI; CD59 complement fragment; CEP-7055; Col 3; combretastatin A-4; endostatin (collagen X VIII fragment); fibronectin fragment; Gro-beta; halofuginone; heparinase; heparin hexasaccharide fragment; HMV833; human chorionic gonadotropin (hCG); IM-862; interferon alpha/beta/gamma; interferon derived protein (IP-10); interleukin-12; Kringle 5 (plasminogen fragment); marimastat; dexamethasone; metalloproteinase inhibitor (TIMP); 2-methoxyestradiol; MMI 270(CGS 27023A); MoAb IMC-1C11; neovastat; NM-3; Panzem; PI-88; placenta ribonuclease inhibitor; plasminogen activator inhibitor; platelet factor-4 (PF4); prinomastat; prolactin 16 kD fragment; proliferin-related protein (PRP); PTK 787/ZK 222594; retinoid sorimastat; squalamine; SS 3304; SU 5416; SU6668; SU11248; tetrahydrocortisol-S; tetrathiomolybdate; Thalidomide; Thrombospondin)-1(TSP-1); TNP-470; transforming growth factor-beta (TGF-b); vasculostatin; vasostatin (calreticulin fragment); ZD6126; ZD6474; farnesyl transferase inhibitor (FTI); and bisphosphonate (for example, alendronate, etidronate, pamidronate, resedronate, ibandronate, zoledronate, olpadronate, icandronate or neridronate), and the like, but are not limited thereto.

There is provided a method for prevention or treatment of angiogenesis-related diseases, including administering a therapeutically effective amount of fusion polypeptide to a subject.

Further, there is provided a method for inhibiting angiogenesis and/or lymphangiogenesis, including administering an effective amount of fusion polypeptide to a subj ect.

Further, there is provided a method for inhibiting proliferation and/or metastasis of cancer, including administering an effective amount of fusion polypeptide to a subject.

Further, there is provided a use of the fusion polypeptide for prevention and/or treatment of neovascular diseases, or use of the fusion polypeptide in the preparation of medicine for prevention and/or treatment of neovascular diseases.

As used herein, the term "administration" refers to supplying a material to a patient by any appropriate method, and the composition may be orally or parenterally administered via common routes capable of reaching to a target tissue. The parenteral administration may include intravenous injection, subcutaneous injection, intramuscular injection, intraperitoneal injection, endothelial administration, local administration, intranasal administration, intrapulmonary administration and intrarectal administration, and the like. For oral administration, oral compositions should be formulated so as to be protected from degradation in the stomach or active agent should be coated, because protein or peptide is digested. And, the composition may be administered by any devices capable of delivering the composition to target cells.

As used herein, the term 'subject' includes human, monkeys, cows, horses, sheep, pigs, chicken, turkeys, common quails, cats, dogs, mice, rabbits or Guinea pigs, but is not limited thereto. According to one example, it is mammals, and according to another example, it is human being.

As used herein, the term "therapeutically effective amount" or "effective amount" refers to an amount of fusion polypeptide effective for treating or preventing target diseases. The suitable administration amount of the pharmaceutical composition may be variously prescribed according to factors such as a formulation method, administration method, age, weight, gender and illness state of a patient, food, administration time, administration route, excretion rate and reaction sensitivity. Preferable administration amount of the composition may be in the range of 1 to 100 mg/kg for adults, but is not limited thereto.

The composition may be administered as a single therapeutic agent or in combination with other therapeutic agents, may be administered sequentially or simultaneously with conventional therapeutic agents, and may be administered once or multiple times. Considering these, it is important to administer an amount capable of obtaining maximum effect with minimum amount, which may be easily determined by one of ordinary knowledge in the art.

There is provided a fusion polypeptide that simultaneously inhibits binding to angiopoietin 2 performing an important function for aging and stabilization of new blood vessels, and VEGF-C and/or -D involved in lymphangiogenesis, and by blocking their signal transduction in cancer cells through the activation of these receptors, effects of inhibiting growth of cancer tissue through angiogenesis and metastasis of tumor through lymphatic vessels may be anticipated.

One or more embodiments will now be described in further detail with reference to the following Examples. However, these examples are for the illustrative purposes only and are not intended to limit the scope of the invention.

Example 1. Construction of Fusion Polypeptide

For the construction of V-body, Ig-like domain 2 of VEGFR2 (R2-2, amino acid residues 120th-220th) and Ig-like domain 2 of VEGFR3 (R3-2, amino acid residues 136th-226th) (SEQ ID NO: 4) were connected, and the gene sequence was optimized so as to be produced in human cells and synthesized by Bioneer (Korea). Tie2 extracellular domain (Tie2-ECD) corresponds to 1st-345th (SEQ ID NO:5) in amino acid sequence of Tie2 (GenBank: AAH35514.2; SEQ ID NO: 1), and the gene sequence follows BC035514.1. The amino acid sequence of VEGFR2 follows NP 002244.1 (SEQ ID NO: 2), the amino acid sequence of VEGFR-3 follows NP 891555.2 (SEQ ID NO: 3), and the gene sequences were optimized so as to be produced in human cells and synthesized by Bioneer. For the construction of AV-body 1, Tie2-ECD, and Ig-like domains 2, 3 of VEGFR-2 (R2-2, R2-3, amino acid residues 123th-326th) were sequentially connected (SEQ ID NO: 6), and for the construction of AV-body 2, Tie2-ECD, R2-2, and R3-2 were sequentially connected (SEQ ID NO: 7).

The prepared nucleic acid fragments were respectively subcloned in a pFUSE-hIgG1-Fc1 vector (InvivoGen) that is constructed so as to fuse the Fc fragment of human IgG1 to C-terminus of target protein. V-body was constructed by subcloning the nucleic acid fragments of R2-2 and R3-2 in the vector using an EcoRI/XhoI restriction enzyme (NEB), and AV-body 1 was constructed by first subcloning the nucleic acid fragments of R2-2 and R2-3 in the vector using an EcoRI/XhoI restriction enzyme, and then, sequentially subcloning the nucleic acid fragment of Tie2-ECD using an AgeI/EcoRI restriction enzyme. AV-body 2 was constructed by subcloning the nucleic acid fragment of Tie2-ECD in the above manufactured V-body construct using an AgeI/EcoRI restriction enzyme.

Example 2. Expression and Purification of Fusion Polypeptide

A nucleic acid molecule coding the fusion polypeptide manufactured in Example 1 was transfected into 293-F cells (Invitrogen) using a Max transfection reagent (Invitrogen). The cells were cultured by agitating at 37° C., 8% $CO_2$, 130 rpm in serum-free 293-F expression medium (Invitrogen), and on the fifth day, the culture solution was recovered.

Figure 3:
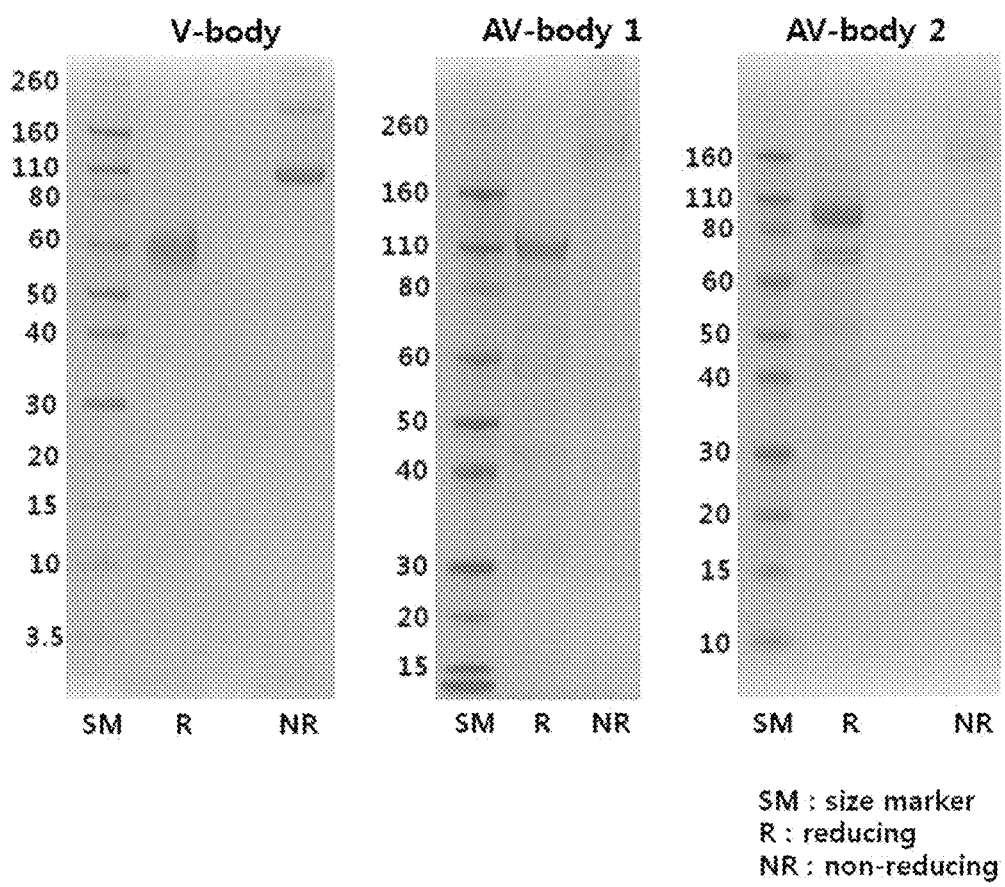
FIG. 3 is a series of three photographs of SDS-PAGE gels confirming the expression of fusion polypeptides V-body, AV-body 1, and AV-body 2 according to Example 2.

From the culture solution obtained by centrifugation of the cultured cells, Fc-fused fusion polypeptide was selectively separated using MabSelectSuRe column (GE Healthcare), and eluted with a 20 mM sodium citrate (pH 3.0) solution, and then, neutralized using a 1 M Tris (pH 9.0) solution. The separated and purified fusion polypeptides were respectively quantified using NanoDrop (Thermo Scientific), and the size and purity were confirmed under reducing, non-reducing conditions through SDS-PAGE (FIG. 3).

Example 3. Measurement of Binding Capacity of Fusion Polypeptide to Ang2, VEGF-C, VEGF-D To measure binding capacities of fusion polypeptides to each target, ELISA (Enzyme-linked immunosorbent assay) was conducted. On a 96-well MaxiSorp™ flat-bottom plate (Nunc), 50 ul of human VEGF-C, VEGF-D, or Ang2 (R&D Systems) were coated in the concentration of 5 ug/ul. And then, the plate was washed 5 times with PBS containing 0.05% Tween-20, and then, blocked with PBS containing 1% BSA at room temperature for 2 hours. 50 ul of each fusion polypeptide was put in each well according to concentration, and then, the plate was incubated at room temperature for 2 hours. And then, it was washed 5 times with PBS containing 0.05% Tween-20, and then, HRP-conjugated anti-human Fc antibody (Sigma) was diluted to 1:5,000 with PBS containing 1% BSA and reacted at room temperature for 1 hour, and washed 5 times with PBS containing 0.1% Tween-20. Finally, to each well of the plate, 50 µl of TMB substrate (SIGMA) was added to cause color reaction, and then, the reaction was stopped with 50 µl of a 5N $H_2SO_4$ solution, and OD450 value was measured on a plate reader (Molecular Devices). Thereby, binding capacities ($K_D$) of the manufactured fusion polypeptides to human VEGF-C, VEGF-D or Ang2 protein were measured. The results are described in the following Table 1. As shown in Table 1, V-body binds to VEGF-C and VEGF-D but does not binds to Ang2, whereas both AV-body 1 and AV-body-2 bind simultaneously to Ang2, VEGF-C and VEGF-D.

TABLE 1

| Name | Ang2 ($K_D$, nM) | VEGF-C ($K_D$, nM) | VEGF-D ($K_D$, nM) |
|---|---|---|---|
| V-body | — | 100 | 100 |
| AV-body 1 | 45 | 130 | 170 |
| AV-body 2 | 20 | 34 | 42 |

Example 4. Effect of Inhibiting Cell Migration of Fusion Polypeptide

Figure 4:
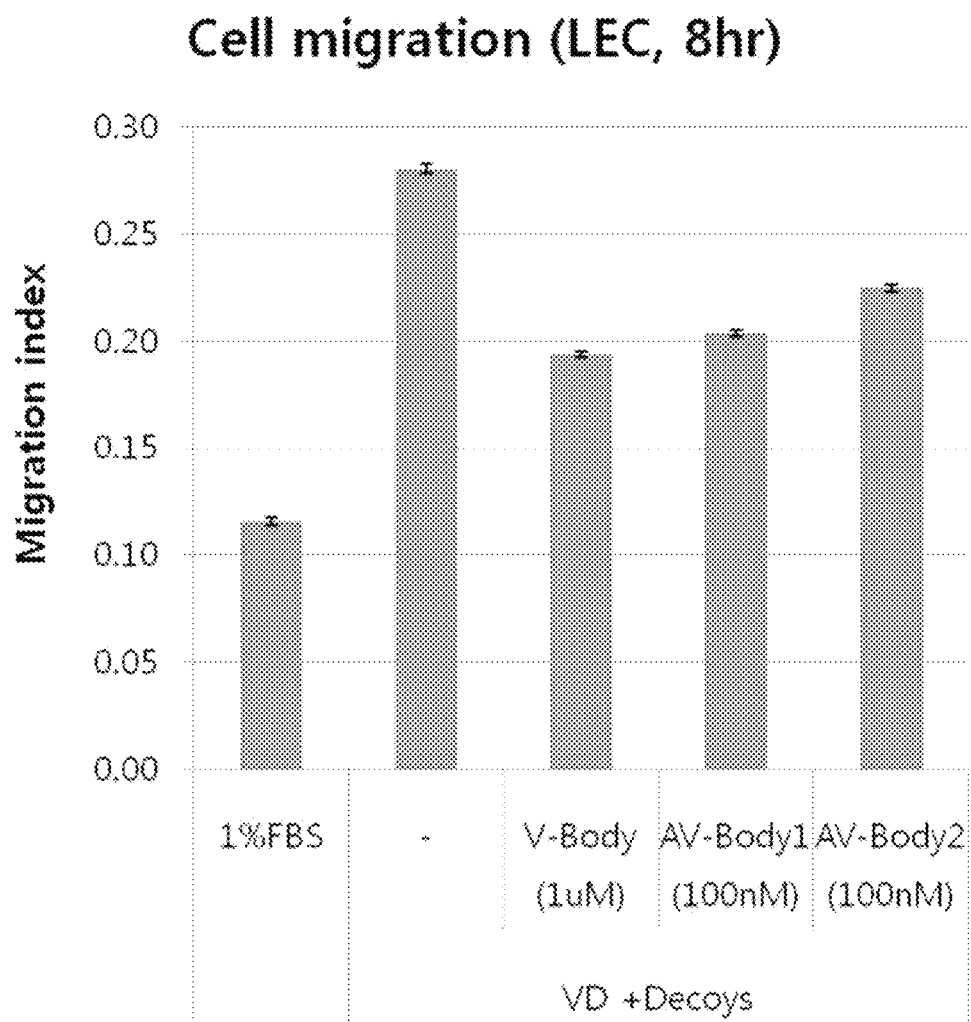
FIG. 4 is a graph showing the effects of three fusion polypeptides (V-body, AV-body 1, AV-body 2) on migration inhibition of lymphatic endothelial cells(LEC) due to VEGF-D.

The migration of lymphatic endothelial cells was measured using xCelligence RTCA (Realtime cell analyzer) of GE Healthcare. RTCA is non-invasive cell monitoring system capable of confirming change in cells by measuring impedance in real-time. To conduct cell migration assay, CIM-plate16 (GE Healthcare) consisting of a lower chamber and an upper chamber is used wherein microelectrodes for measuring impedance are arranged in the upper chamber, and if cells seeded in the chamber migrate through microholes, they are attached to the microelectrode, thus allowing confirmation of migration of cells, which was represented by migration index. Lymphatic endothelial cells (P5-7) that were grown in EGM2-MV medium was grown for 6 hours in EBM medium to which 1% FBS is added. Into each well of the lower chamber of CIM-plate16, 2 ug/ml VEGF-D and fusion polypeptide were put in EBM medium containing 1% FBS, and then, assembled with the upper chamber coated with fibronectin. 30 ul of serum-free EBM medium was introduced in the upper chamber, and then, put in an incubator for 1 hour for equilibration between the plate and the medium, a CIM-plate was installed in a device station in the incubator, and background value was measured. Lymphatic endothelial cells resuspended in serum-free medium were seeded at 40,000~60,000 cells/well, left to settle down for 15 minutes, and then, installed in a device to measure cell migration in real-time. The migration degree of cells was represented by Migration index, and it was confirmed that all the three fusion polypeptides inhibit migration of lymphatic endothelial cells by VEGF-D (FIG. 4).

Figure 5:
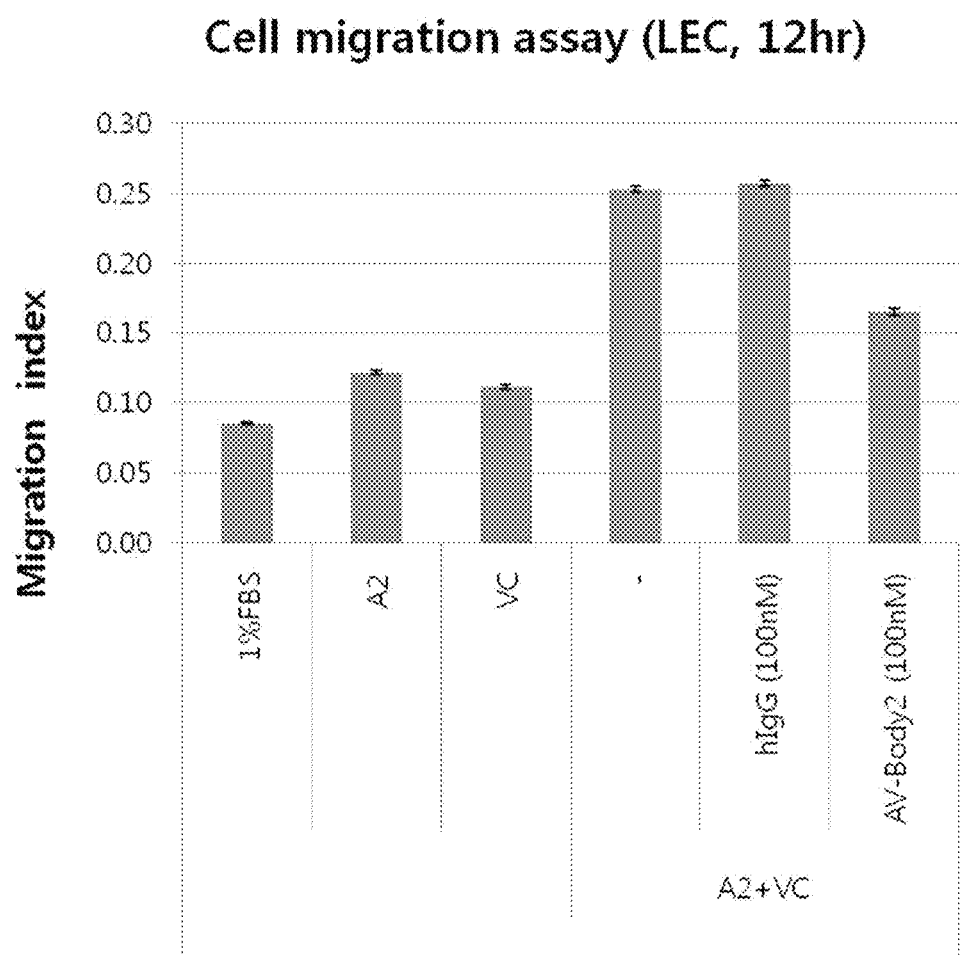
FIG. 5 is a graph showing the effect of fusion polypeptide AV-body 2 on migration inhibition of lymphatic endothelial cells(LEC) due to VEGF-C("VC") and Ang2("A2").

It was also confirmed that if VEGF-C and Ang2 are treated together by the same experiment method as above, migration of lymphatic endothelial cells are more increased than single treatment group of each growth factor, and that AV-Body 2 inhibit migration of lymphatic endothelial cells by the combined effect of VEGF-C and Ang2 (FIG. 5).

Example 5. Inhibition Effect of Cell Proliferation of Fusion Polypeptide

Figure 6:
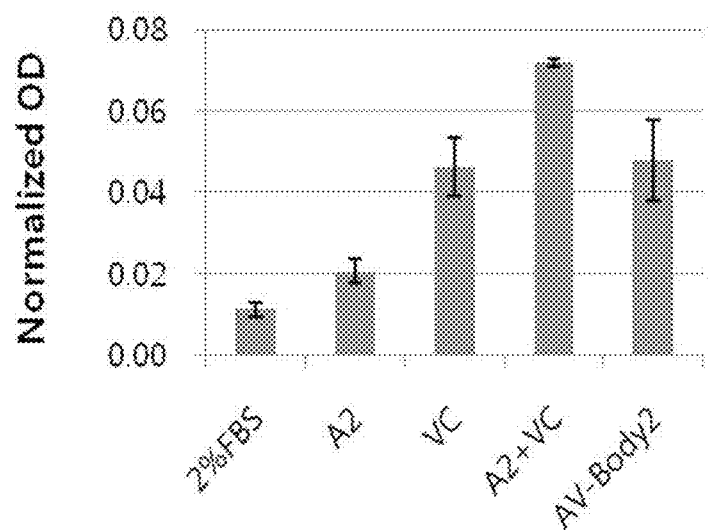
FIG. 6 provides a graph (A) showing the effect of fusion polypeptide AV-body 2 for inhibiting proliferation of lymphatic endothelial cells(LEC) due to VEGF-C("VC") and Ang2("A2"), and a graph (B) showing the effect of fusion polypeptide AV-body 2 for inhibiting proliferation of vascular endothelial cells(VEC) due to VEGF-C("VC") and Ang2("A2").
Figure 6:
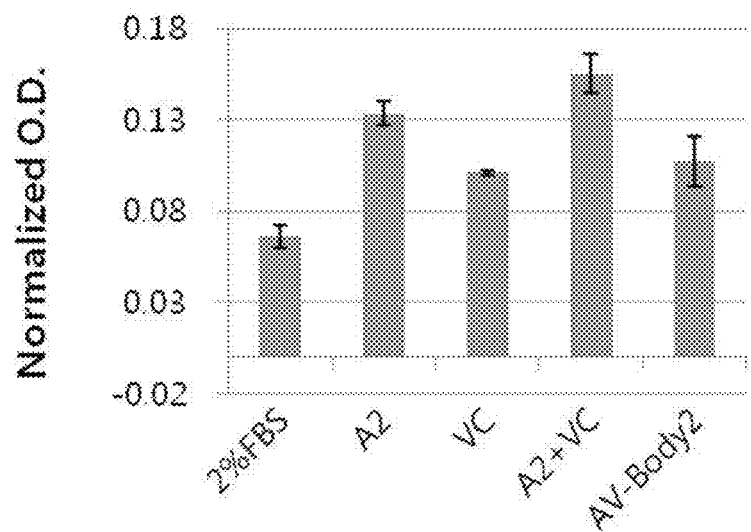

Proliferation of vascular and lymphatic endothelial cells were measured using Cell counting kit-8 (Dojindo Molecular Technology). P3~P8 vascular endothelial cells or lymphatic endothelial cells were put in a Collagen coated 96 well plate (BD Bioscience) at 3,000~5,000 cells/well, and then cultured. And, 2 ug/ml Ang2 and 1 ug/ml VEGF-C were sequentially or simultaneously mixed with serum-free medium, and then, fusion polypeptide AV-Body 2 was introduced into the medium. After removing the culture solution of 96-well plate, the plate was washed with PBS, and then, medium containing growth factor and fusion polypeptide (AV-Body 2) was added, and cultured for 3 days. For CCK-8 assay, 10 ul of the solution was added and cultured for 1 hour, and then, absorbance was measured at 450 nm using a Microplate reader (Perkin Elmer). As the result, as shown in FIG. 6, it was confirmed that in both of vascular endothelial cells and lymphatic endothelial cells, cell proliferation was higher in combined treatment group than in each single treatment group of VEGF-C and Ang2, and that cell proliferation by VEGF-C and Ang2 was inhibited by AV-Body 2.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A fusion polypeptide capable of binding simultaneously to VEGF-C and VEGF-D, comprising a VEGFR2 extracellular domain, a VEGFR3 extracellular domain, and the Fc region of an immunoglobulin, wherein the VEGFR2 extracellular domain comprises Ig-like domain 2, and the VEGFR3 extracellular domain comprises Ig-like domain 2.

2. The fusion polypeptide according to claim 1, wherein the fusion polypeptide comprises a VEGFR2 extracellular domain comprising amino acid residues 120-220 of SEQ ID NO: 2, a VEGFR3 extracellular domain comprising amino acid residues 136-226 of SEQ ID NO: 3, and the Fc region of an immunoglobulin.

3. The fusion polypeptide according to claim 1, wherein the fusion polypeptide comprises a polypeptide consisting of the amino acid sequence of SEQ ID NO: 4, and the Fc region of immunoglobulin.

4. A pharmaceutical composition comprising the fusion polypeptide of claim 1.

5. A method for treating a neovascular disease, inhibiting angiogenesis or lymphangiogenesis, or inhibiting proliferation and metastasis of cancer, comprising administering a therapeutically effective amount of the fusion polypeptide of claim 1 to a subject in need thereof.

* * * * *

```
                              SEQUENCE LISTING

<160> NUMBER OF SEQ ID NOS: 7

<210> SEQ ID NO 1
<211> LENGTH: 1124
<212> TYPE: PRT
<213> ORGANISM: Artificial Sequence
<220> FEATURE:
<223> OTHER INFORMATION: Synthetic (Tie2)

<400> SEQUENCE: 1

Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
                20                  25                  30

Pro Leu Val Ser Asp Ala Glu Thr Ser Leu Thr Cys Ile Ala Ser Gly
            35                  40                  45

Trp Arg Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
    210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270
```

```
Gly Cys Lys Ser Tyr Val Phe Cys Leu Pro Asp Pro Tyr Gly Cys Ser
            275                 280                 285

Cys Ala Thr Gly Trp Lys Gly Leu Gln Cys Asn Glu Ala Cys His Pro
290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Pro Arg Met Thr Pro Lys Ile
                340                 345                 350

Val Asp Leu Pro Asp His Ile Glu Val Asn Ser Gly Lys Phe Asn Pro
            355                 360                 365

Ile Cys Lys Ala Ser Gly Trp Pro Leu Pro Thr Asn Glu Glu Met Thr
370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                405                 410                 415

Pro Asp Ser Gly Val Trp Val Cys Ser Val Asn Thr Val Ala Gly Met
            420                 425                 430

Val Glu Lys Pro Phe Asn Ile Ser Val Lys Val Leu Pro Lys Pro Leu
            435                 440                 445

Asn Ala Pro Asn Val Ile Asp Thr Gly His Asn Phe Ala Val Ile Asn
            450                 455                 460

Ile Ser Ser Glu Pro Tyr Phe Gly Asp Gly Pro Ile Lys Ser Lys Lys
465                 470                 475                 480

Leu Leu Tyr Lys Pro Val Asn His Tyr Glu Ala Trp Gln His Ile Gln
                485                 490                 495

Val Thr Asn Glu Ile Val Thr Leu Asn Tyr Leu Glu Pro Arg Thr Glu
            500                 505                 510

Tyr Glu Leu Cys Val Gln Leu Val Arg Arg Gly Glu Gly Gly Glu Gly
            515                 520                 525

His Pro Gly Pro Val Arg Arg Phe Thr Thr Ala Ser Ile Gly Leu Pro
530                 535                 540

Pro Pro Arg Gly Leu Asn Leu Leu Pro Lys Ser Gln Thr Thr Leu Asn
545                 550                 555                 560

Leu Thr Trp Gln Pro Ile Phe Pro Ser Ser Glu Asp Asp Phe Tyr Val
                565                 570                 575

Glu Val Glu Arg Arg Ser Val Gln Lys Ser Asp Gln Asn Ile Lys
                580                 585                 590

Val Pro Gly Asn Leu Thr Ser Val Leu Leu Asn Asn Leu His Pro Arg
            595                 600                 605

Glu Gln Tyr Val Val Arg Ala Arg Val Asn Thr Lys Ala Gln Gly Glu
            610                 615                 620

Trp Ser Glu Asp Leu Thr Ala Trp Thr Leu Ser Asp Ile Leu Pro Pro
625                 630                 635                 640

Gln Pro Glu Asn Ile Lys Ile Ser Asn Ile Thr His Ser Ser Ala Val
                645                 650                 655

Ile Ser Trp Thr Ile Leu Asp Gly Tyr Ser Ile Ser Ser Ile Thr Ile
                660                 665                 670

Arg Tyr Lys Val Gln Gly Lys Asn Glu Asp Gln His Val Asp Val Lys
            675                 680                 685
```

-continued

Ile Lys Asn Ala Thr Ile Thr Gln Tyr Gln Leu Lys Gly Leu Glu Pro
690                 695                 700

Glu Thr Ala Tyr Gln Val Asp Ile Phe Ala Glu Asn Asn Ile Gly Ser
705                 710                 715                 720

Ser Asn Pro Ala Phe Ser His Glu Leu Val Thr Leu Pro Glu Ser Gln
            725                 730                 735

Ala Pro Ala Asp Leu Gly Gly Lys Met Leu Leu Ile Ala Ile Leu
            740                 745                 750

Gly Ser Ala Gly Met Thr Cys Leu Thr Val Leu Leu Ala Phe Leu Ile
            755                 760                 765

Ile Leu Gln Leu Lys Arg Ala Asn Val Gln Arg Arg Met Ala Gln Ala
770                 775                 780

Phe Gln Asn Val Arg Glu Pro Ala Val Gln Phe Asn Ser Gly Thr
785                 790                 795                 800

Leu Ala Leu Asn Arg Lys Val Lys Asn Asn Pro Asp Pro Thr Ile Tyr
                805                 810                 815

Pro Val Leu Asp Trp Asn Asp Ile Lys Phe Gln Asp Val Ile Gly Glu
            820                 825                 830

Gly Asn Phe Gly Gln Val Leu Lys Ala Arg Ile Lys Lys Asp Gly Leu
            835                 840                 845

Arg Met Asp Ala Ala Ile Lys Arg Met Lys Glu Tyr Ala Ser Lys Asp
850                 855                 860

Asp His Arg Asp Phe Ala Gly Glu Leu Glu Val Leu Cys Lys Leu Gly
865                 870                 875                 880

His His Pro Asn Ile Ile Asn Leu Leu Gly Ala Cys Glu His Arg Gly
                885                 890                 895

Tyr Leu Tyr Leu Ala Ile Glu Tyr Ala Pro His Gly Asn Leu Leu Asp
            900                 905                 910

Phe Leu Arg Lys Ser Arg Val Leu Glu Thr Asp Pro Ala Phe Ala Ile
            915                 920                 925

Ala Asn Ser Thr Ala Ser Thr Leu Ser Ser His His Leu Leu His Phe
930                 935                 940

Ala Ala Asp Val Ala Arg Gly Met Asp Tyr Leu Ser Gln Lys Gln Phe
945                 950                 955                 960

Ile His Arg Asp Leu Ala Ala Arg Asn Ile Leu Val Gly Glu Asn Tyr
            965                 970                 975

Val Ala Lys Ile Ala Asp Phe Gly Leu Ser Arg Gly Gln Glu Val Tyr
            980                 985                 990

Val Lys Lys Thr Met Gly Arg Leu Pro Val Arg Trp Met Ala Ile Glu
            995                 1000                1005

Ser Leu Asn Tyr Ser Val Tyr Thr Thr Asn Ser Asp Val Trp Ser
        1010                1015                1020

Tyr Gly Val Leu Leu Trp Glu Ile Val Ser Leu Gly Gly Thr Pro
        1025                1030                1035

Tyr Cys Gly Met Thr Cys Ala Glu Leu Tyr Glu Lys Leu Pro Gln
        1040                1045                1050

Gly Tyr Arg Leu Glu Lys Pro Leu Asn Cys Asp Asp Glu Val Tyr
        1055                1060                1065

Asp Leu Met Arg Gln Cys Trp Arg Glu Lys Pro Tyr Glu Arg Pro
        1070                1075                1080

Ser Phe Ala Gln Ile Leu Val Ser Leu Asn Arg Met Leu Glu Glu
        1085                1090                1095

Arg Lys Thr Tyr Val Asn Thr Thr Leu Tyr Glu Lys Phe Thr Tyr

```
            1100              1105            1110
Ala Gly Ile Asp Cys Ser Ala  Glu Glu Ala Ala
        1115             1120

<210> SEQ ID NO 2
<211> LENGTH: 1356
<212> TYPE: PRT
<213> ORGANISM: Artificial Sequence
<220> FEATURE:
<223> OTHER INFORMATION: Synthetic (VEGRF-2)

<400> SEQUENCE: 2

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
```

-continued

```
            340                 345                 350
Lys Tyr Leu Gly Tyr Pro Pro Glu Ile Lys Trp Tyr Lys Asn Gly
            355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
                420                 425                 430

Asp Ser Tyr Gln Tyr Gly Thr Thr Gln Thr Leu Thr Cys Thr Val Tyr
            435                 440                 445

Ala Ile Pro Pro Pro His His Ile His Trp Tyr Trp Gln Leu Glu Glu
            450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
                500                 505                 510

Thr Val Ser Thr Leu Val Ile Gln Ala Ala Asn Val Ser Ala Leu Tyr
            515                 520                 525

Lys Cys Glu Ala Val Asn Lys Val Gly Arg Gly Glu Arg Val Ile Ser
            530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
                580                 585                 590

Ile His Val Gly Glu Leu Pro Thr Pro Val Cys Lys Asn Leu Asp Thr
            595                 600                 605

Leu Trp Lys Leu Asn Ala Thr Met Phe Ser Asn Ser Thr Asn Asp Ile
            610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655

Arg Gln Leu Thr Val Leu Glu Arg Val Ala Pro Thr Ile Thr Gly Asn
                660                 665                 670

Leu Glu Asn Gln Thr Thr Ser Ile Gly Glu Ser Ile Glu Val Ser Cys
            675                 680                 685

Thr Ala Ser Gly Asn Pro Pro Pro Gln Ile Met Trp Phe Lys Asp Asn
            690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
                740                 745                 750

Ile Ile Glu Gly Ala Gln Glu Lys Thr Asn Leu Glu Ile Ile Ile Leu
            755                 760                 765
```

-continued

```
Val Gly Thr Ala Val Ile Ala Met Phe Phe Trp Leu Leu Val Ile
    770                 775                 780
Ile Leu Arg Thr Val Lys Arg Ala Asn Gly Gly Glu Leu Lys Thr Gly
785                 790                 795                 800
Tyr Leu Ser Ile Val Met Asp Pro Asp Glu Leu Pro Leu Asp Glu His
                805                 810                 815
Cys Glu Arg Leu Pro Tyr Asp Ala Ser Lys Trp Glu Phe Pro Arg Asp
                820                 825                 830
Arg Leu Lys Leu Gly Lys Pro Leu Gly Arg Gly Ala Phe Gly Gln Val
                835                 840                 845
Ile Glu Ala Asp Ala Phe Gly Ile Asp Lys Thr Ala Thr Cys Arg Thr
    850                 855                 860
Val Ala Val Lys Met Leu Lys Glu Gly Ala Thr His Ser Glu His Arg
865                 870                 875                 880
Ala Leu Met Ser Glu Leu Lys Ile Leu Ile His Ile Gly His His Leu
                885                 890                 895
Asn Val Val Asn Leu Leu Gly Ala Cys Thr Lys Pro Gly Gly Pro Leu
                900                 905                 910
Met Val Ile Val Glu Phe Cys Lys Phe Gly Asn Leu Ser Thr Tyr Leu
    915                 920                 925
Arg Ser Lys Arg Asn Glu Phe Val Pro Tyr Lys Thr Lys Gly Ala Arg
    930                 935                 940
Phe Arg Gln Gly Lys Asp Tyr Val Gly Ala Ile Pro Val Asp Leu Lys
945                 950                 955                 960
Arg Arg Leu Asp Ser Ile Thr Ser Ser Gln Ser Ala Ser Ser Gly
                965                 970                 975
Phe Val Glu Glu Lys Ser Leu Ser Asp Val Glu Glu Glu Glu Ala Pro
                980                 985                 990
Glu Asp Leu Tyr Lys Asp Phe Leu Thr Leu Glu His Leu Ile Cys Tyr
                995                 1000                1005
Ser Phe Gln Val Ala Lys Gly Met Glu Phe Leu Ala Ser Arg Lys
    1010                1015                1020
Cys Ile His Arg Asp Leu Ala Ala Arg Asn Ile Leu Leu Ser Glu
    1025                1030                1035
Lys Asn Val Val Lys Ile Cys Asp Phe Gly Leu Ala Arg Asp Ile
    1040                1045                1050
Tyr Lys Asp Pro Asp Tyr Val Arg Lys Gly Asp Ala Arg Leu Pro
    1055                1060                1065
Leu Lys Trp Met Ala Pro Glu Thr Ile Phe Asp Arg Val Tyr Thr
    1070                1075                1080
Ile Gln Ser Asp Val Trp Ser Phe Gly Val Leu Leu Trp Glu Ile
    1085                1090                1095
Phe Ser Leu Gly Ala Ser Pro Tyr Pro Gly Val Lys Ile Asp Glu
    1100                1105                1110
Glu Phe Cys Arg Arg Leu Lys Glu Gly Thr Arg Met Arg Ala Pro
    1115                1120                1125
Asp Tyr Thr Thr Pro Glu Met Tyr Gln Thr Met Leu Asp Cys Trp
    1130                1135                1140
His Gly Glu Pro Ser Gln Arg Pro Thr Phe Ser Glu Leu Val Glu
    1145                1150                1155
His Leu Gly Asn Leu Leu Gln Ala Asn Ala Gln Gln Asp Gly Lys
    1160                1165                1170
```

```
Asp Tyr Ile Val Leu Pro Ile Ser Glu Thr Leu Ser Met Glu Glu
    1175                1180                1185

Asp Ser Gly Leu Ser Leu Pro Thr Ser Pro Val Ser Cys Met Glu
    1190                1195                1200

Glu Glu Glu Val Cys Asp Pro Lys Phe His Tyr Asp Asn Thr Ala
    1205                1210                1215

Gly Ile Ser Gln Tyr Leu Gln Asn Ser Lys Arg Lys Ser Arg Pro
    1220                1225                1230

Val Ser Val Lys Thr Phe Glu Asp Ile Pro Leu Glu Glu Pro Glu
    1235                1240                1245

Val Lys Val Ile Pro Asp Asp Asn Gln Thr Asp Ser Gly Met Val
    1250                1255                1260

Leu Ala Ser Glu Glu Leu Lys Thr Leu Glu Asp Arg Thr Lys Leu
    1265                1270                1275

Ser Pro Ser Phe Gly Gly Met Val Pro Ser Lys Ser Arg Glu Ser
    1280                1285                1290

Val Ala Ser Glu Gly Ser Asn Gln Thr Ser Gly Tyr Gln Ser Gly
    1295                1300                1305

Tyr His Ser Asp Asp Thr Asp Thr Thr Val Tyr Ser Ser Glu Glu
    1310                1315                1320

Ala Glu Leu Leu Lys Leu Ile Glu Ile Gly Val Gln Thr Gly Ser
    1325                1330                1335

Thr Ala Gln Ile Leu Gln Pro Asp Ser Gly Thr Thr Leu Ser Ser
    1340                1345                1350

Pro Pro Val
    1355

<210> SEQ ID NO 3
<211> LENGTH: 1363
<212> TYPE: PRT
<213> ORGANISM: Artificial Sequence
<220> FEATURE:
<223> OTHER INFORMATION: Synthetic (VEGFR-3)

<400> SEQUENCE: 3

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
                20                  25                  30

Asn Ile Thr Glu Glu Ser His Val Ile Asp Thr Gly Asp Ser Leu Ser
            35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
    130                 135                 140

Thr Leu Leu Val Asn Arg Lys Asp Ala Met Trp Val Pro Cys Leu Val
145                 150                 155                 160
```

```
Ser Ile Pro Gly Leu Asn Val Thr Leu Arg Ser Gln Ser Ser Val Leu
            165                 170                 175
Trp Pro Asp Gly Gln Glu Val Val Trp Asp Asp Arg Arg Gly Met Leu
        180                 185                 190
Val Ser Thr Pro Leu Leu His Asp Ala Leu Tyr Leu Gln Cys Glu Thr
        195                 200                 205
Thr Trp Gly Asp Gln Asp Phe Leu Ser Asn Pro Phe Leu Val His Ile
    210                 215                 220
Thr Gly Asn Glu Leu Tyr Asp Ile Gln Leu Leu Pro Arg Lys Ser Leu
225                 230                 235                 240
Glu Leu Leu Val Gly Glu Lys Leu Val Leu Asn Cys Thr Val Trp Ala
                245                 250                 255
Glu Phe Asn Ser Gly Val Thr Phe Asp Trp Asp Tyr Pro Gly Lys Gln
            260                 265                 270
Ala Glu Arg Gly Lys Trp Val Pro Glu Arg Arg Ser Gln Gln Thr His
        275                 280                 285
Thr Glu Leu Ser Ser Ile Leu Thr Ile His Asn Val Ser Gln His Asp
    290                 295                 300
Leu Gly Ser Tyr Val Cys Lys Ala Asn Asn Gly Ile Gln Arg Phe Arg
305                 310                 315                 320
Glu Ser Thr Glu Val Ile Val His Glu Asn Pro Phe Ile Ser Val Glu
                325                 330                 335
Trp Leu Lys Gly Pro Ile Leu Glu Ala Thr Ala Gly Asp Glu Leu Val
            340                 345                 350
Lys Leu Pro Val Lys Leu Ala Ala Tyr Pro Pro Pro Glu Phe Gln Trp
        355                 360                 365
Tyr Lys Asp Gly Lys Ala Leu Ser Gly Arg His Ser Pro His Ala Leu
    370                 375                 380
Val Leu Lys Glu Val Thr Glu Ala Ser Thr Gly Thr Tyr Thr Leu Ala
385                 390                 395                 400
Leu Trp Asn Ser Ala Ala Gly Leu Arg Arg Asn Ile Ser Leu Glu Leu
                405                 410                 415
Val Val Asn Val Pro Pro Gln Ile His Glu Lys Glu Ala Ser Ser Pro
            420                 425                 430
Ser Ile Tyr Ser Arg His Ser Arg Gln Ala Leu Thr Cys Thr Ala Tyr
        435                 440                 445
Gly Val Pro Leu Pro Leu Ser Ile Gln Trp His Trp Arg Pro Trp Thr
    450                 455                 460
Pro Cys Lys Met Phe Ala Gln Arg Ser Leu Arg Arg Arg Gln Gln Gln
465                 470                 475                 480
Asp Leu Met Pro Gln Cys Arg Asp Trp Arg Ala Val Thr Thr Gln Asp
                485                 490                 495
Ala Val Asn Pro Ile Glu Ser Leu Asp Thr Trp Thr Glu Phe Val Glu
            500                 505                 510
Gly Lys Asn Lys Thr Val Ser Lys Leu Val Ile Gln Asn Ala Asn Val
        515                 520                 525
Ser Ala Met Tyr Lys Cys Val Val Ser Asn Lys Val Gly Gln Asp Glu
    530                 535                 540
Arg Leu Ile Tyr Phe Tyr Val Thr Thr Ile Pro Asp Gly Phe Thr Ile
545                 550                 555                 560
Glu Ser Lys Pro Ser Glu Glu Leu Leu Glu Gly Gln Pro Val Leu Leu
                565                 570                 575
Ser Cys Gln Ala Asp Ser Tyr Lys Tyr Glu His Leu Arg Trp Tyr Arg
```

```
            580                 585                 590
Leu Asn Leu Ser Thr Leu His Asp Ala His Gly Asn Pro Leu Leu Leu
            595                 600                 605

Asp Cys Lys Asn Val His Leu Phe Ala Thr Pro Leu Ala Ala Ser Leu
            610                 615                 620

Glu Val Ala Pro Gly Ala Arg His Ala Thr Leu Ser Leu Ser Ile
625                 630                 635                 640

Pro Arg Val Ala Pro Glu His Glu Gly His Tyr Val Cys Glu Val Gln
                    645                 650                 655

Asp Arg Arg Ser His Asp Lys His Cys His Lys Lys Tyr Leu Ser Val
                    660                 665                 670

Gln Ala Leu Glu Ala Pro Arg Leu Thr Gln Asn Leu Thr Asp Leu Leu
            675                 680                 685

Val Asn Val Ser Asp Ser Leu Glu Met Gln Cys Leu Val Ala Gly Ala
            690                 695                 700

His Ala Pro Ser Ile Val Trp Tyr Lys Asp Glu Arg Leu Leu Glu Glu
705                 710                 715                 720

Lys Ser Gly Val Asp Leu Ala Asp Ser Asn Gln Lys Leu Ser Ile Gln
                    725                 730                 735

Arg Val Arg Glu Glu Asp Ala Gly Arg Tyr Leu Cys Ser Val Cys Asn
                    740                 745                 750

Ala Lys Gly Cys Val Asn Ser Ser Ala Ser Val Ala Val Glu Gly Ser
                    755                 760                 765

Glu Asp Lys Gly Ser Met Glu Ile Val Ile Leu Val Gly Thr Gly Val
770                 775                 780

Ile Ala Val Phe Phe Trp Val Leu Leu Leu Ile Phe Cys Asn Met
785                 790                 795                 800

Arg Arg Pro Ala His Ala Asp Ile Lys Thr Gly Tyr Leu Ser Ile Ile
                    805                 810                 815

Met Asp Pro Gly Glu Val Pro Leu Glu Glu Gln Cys Glu Tyr Leu Ser
                    820                 825                 830

Tyr Asp Ala Ser Gln Trp Glu Phe Pro Arg Glu Arg Leu His Leu Gly
            835                 840                 845

Arg Val Leu Gly Tyr Gly Ala Phe Gly Lys Val Val Glu Ala Ser Ala
            850                 855                 860

Phe Gly Ile His Lys Gly Ser Ser Cys Asp Thr Val Ala Val Lys Met
865                 870                 875                 880

Leu Lys Glu Gly Ala Thr Ala Ser Glu His Arg Ala Leu Met Ser Glu
                    885                 890                 895

Leu Lys Ile Leu Ile His Ile Gly Asn His Leu Asn Val Val Asn Leu
                    900                 905                 910

Leu Gly Ala Cys Thr Lys Pro Gln Gly Pro Leu Met Val Ile Val Glu
            915                 920                 925

Phe Cys Lys Tyr Gly Asn Leu Ser Asn Phe Leu Arg Ala Lys Arg Asp
            930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Pro Gly Ser
                    965                 970                 975

Ser Asp Arg Val Leu Phe Ala Arg Phe Ser Lys Thr Glu Gly Gly Ala
            980                 985                 990

Arg Arg Ala Ser Pro Asp Gln Glu  Ala Glu Asp Leu  Trp  Leu Ser Pro
            995                 1000                1005
```

Leu Thr Met Glu Asp Leu Val Cys Tyr Ser Phe Gln Val Ala Arg
1010                1015                1020

Gly Met Glu Phe Leu Ala Ser Arg Lys Cys Ile His Arg Asp Leu
1025                1030                1035

Ala Ala Arg Asn Ile Leu Leu Ser Glu Ser Asp Val Val Lys Ile
1040                1045                1050

Cys Asp Phe Gly Leu Ala Arg Asp Ile Tyr Lys Asp Pro Asp Tyr
1055                1060                1065

Val Arg Lys Gly Ser Ala Arg Leu Pro Leu Lys Trp Met Ala Pro
1070                1075                1080

Glu Ser Ile Phe Asp Lys Val Tyr Thr Thr Gln Ser Asp Val Trp
1085                1090                1095

Ser Phe Gly Val Leu Leu Trp Glu Ile Phe Ser Leu Gly Ala Ser
1100                1105                1110

Pro Tyr Pro Gly Val Gln Ile Asn Glu Glu Phe Cys Gln Arg Leu
1115                1120                1125

Arg Asp Gly Thr Arg Met Arg Ala Pro Glu Leu Ala Thr Pro Ala
1130                1135                1140

Ile Arg Arg Ile Met Leu Asn Cys Trp Ser Gly Asp Pro Lys Ala
1145                1150                1155

Arg Pro Ala Phe Ser Glu Leu Val Glu Ile Leu Gly Asp Leu Leu
1160                1165                1170

Gln Gly Arg Gly Leu Gln Glu Glu Glu Val Cys Met Ala Pro
1175                1180                1185

Arg Ser Ser Gln Ser Ser Glu Glu Gly Ser Phe Ser Gln Val Ser
1190                1195                1200

Thr Met Ala Leu His Ile Ala Gln Ala Asp Ala Glu Asp Ser Pro
1205                1210                1215

Pro Ser Leu Gln Arg His Ser Leu Ala Ala Arg Tyr Tyr Asn Trp
1220                1225                1230

Val Ser Phe Pro Gly Cys Leu Ala Arg Gly Ala Glu Thr Arg Gly
1235                1240                1245

Ser Ser Arg Met Lys Thr Phe Glu Glu Phe Pro Met Thr Pro Thr
1250                1255                1260

Thr Tyr Lys Gly Ser Val Asp Asn Gln Thr Asp Ser Gly Met Val
1265                1270                1275

Leu Ala Ser Glu Glu Phe Glu Gln Ile Glu Ser Arg His Arg Gln
1280                1285                1290

Glu Ser Gly Phe Ser Cys Lys Gly Pro Gly Gln Asn Val Ala Val
1295                1300                1305

Thr Arg Ala His Pro Asp Ser Gln Gly Arg Arg Arg Arg Pro Glu
1310                1315                1320

Arg Gly Ala Arg Gly Gly Gln Val Phe Tyr Asn Ser Glu Tyr Gly
1325                1330                1335

Glu Leu Ser Glu Pro Ser Glu Glu Asp His Cys Ser Pro Ser Ala
1340                1345                1350

Arg Val Thr Phe Phe Thr Asp Asn Ser Tyr
1355                1360

<210> SEQ ID NO 4
<211> LENGTH: 213
<212> TYPE: PRT
<213> ORGANISM: Artificial Sequence
<220> FEATURE:

<223> OTHER INFORMATION: Synthetic (V-body)

<400> SEQUENCE: 4

```
Met Gln Ser Lys Val Leu Leu Ala Val Ala Leu Trp Leu Cys Val Glu
1               5                   10                  15

Thr Arg Ala Ala Ser Asp Tyr Arg Ser Pro Phe Ile Ala Ser Val Ser
            20                  25                  30

Asp Gln His Gly Val Val Tyr Ile Thr Glu Asn Lys Asn Lys Thr Val
        35                  40                  45

Val Ile Pro Cys Leu Gly Ser Ile Ser Asn Leu Asn Val Ser Leu Cys
    50                  55                  60

Ala Arg Tyr Pro Glu Lys Arg Phe Val Pro Asp Gly Asn Arg Ile Ser
65                  70                  75                  80

Trp Asp Ser Lys Lys Gly Phe Thr Ile Pro Ser Tyr Met Ile Ser Tyr
                85                  90                  95

Ala Gly Met Val Phe Cys Glu Ala Lys Ile Asn Asp Glu Ser Tyr Gln
            100                 105                 110

Ser Ile Met Tyr Ile Val Val Val Gly Glu Gln Pro Phe Ile Asn
        115                 120                 125

Lys Pro Asp Thr Leu Leu Val Asn Arg Lys Asp Ala Met Trp Val Pro
    130                 135                 140

Cys Leu Val Ser Ile Pro Gly Leu Asn Val Thr Leu Arg Ser Gln Ser
145                 150                 155                 160

Ser Val Leu Trp Pro Asp Gly Gln Glu Val Val Trp Asp Asp Arg Arg
                165                 170                 175

Gly Met Leu Val Ser Thr Pro Leu Leu His Asp Ala Leu Tyr Leu Gln
            180                 185                 190

Cys Glu Thr Thr Trp Gly Asp Gln Asp Phe Leu Ser Asn Pro Phe Leu
        195                 200                 205

Val His Ile Thr Gly
    210
```

<210> SEQ ID NO 5
<211> LENGTH: 345
<212> TYPE: PRT
<213> ORGANISM: Artificial Sequence
<220> FEATURE:
<223> OTHER INFORMATION: Synthetic (Tie2 ECD (Extracellular domain))

<400> SEQUENCE: 5

```
Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
        35                  40                  45

Trp Arg Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125
```

```
Leu Thr Met Thr Val Asp Lys Gly Asp Asn Val Asn Ile Ser Phe Lys
            130                 135                 140

Lys Val Leu Ile Lys Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
            195                 200                 205

Arg Arg Cys Glu Ala Gln Lys Trp Gly Pro Glu Cys Asn His Leu Cys
210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
            275                 280                 285

Cys Ala Thr Gly Trp Lys Gly Leu Gln Cys Asn Glu Ala Cys His Pro
290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile
            340                 345

<210> SEQ ID NO 6
<211> LENGTH: 551
<212> TYPE: PRT
<213> ORGANISM: Artificial Sequence
<220> FEATURE:
<223> OTHER INFORMATION: Synthetic (AV-body 1)

<400> SEQUENCE: 6

Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
                20                  25                  30

Pro Leu Val Ser Asp Ala Glu Thr Ser Leu Thr Cys Ile Ala Ser Gly
            35                  40                  45

Trp Arg Pro His Glu Pro Ile Thr Ile Gly Arg Asp Phe Glu Ala Leu
        50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
                100                 105                 110

Ile Arg Thr Met Lys Met Arg Gln Gln Ala Ser Phe Leu Pro Ala Thr
            115                 120                 125

Leu Thr Met Thr Val Asp Lys Gly Asp Asn Val Asn Ile Ser Phe Lys
            130                 135                 140
```

```
Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
    210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
    290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Glu Phe Ser Pro Phe Ile Ala
            340                 345                 350

Ser Val Ser Asp Gln His Gly Val Val Tyr Ile Thr Glu Asn Lys Asn
        355                 360                 365

Lys Thr Val Val Ile Pro Cys Leu Gly Ser Ile Ser Asn Leu Asn Val
    370                 375                 380

Ser Leu Cys Ala Arg Tyr Pro Glu Lys Arg Phe Val Pro Asp Gly Asn
385                 390                 395                 400

Arg Ile Ser Trp Asp Ser Lys Lys Gly Phe Thr Ile Pro Ser Tyr Met
                405                 410                 415

Ile Ser Tyr Ala Gly Met Val Phe Cys Glu Ala Lys Ile Asn Asp Glu
            420                 425                 430

Ser Tyr Gln Ser Ile Met Tyr Ile Val Val Val Gly Tyr Arg Ile
        435                 440                 445

Tyr Asp Val Val Leu Ser Pro Ser His Gly Ile Glu Leu Ser Val Gly
    450                 455                 460

Glu Lys Leu Val Leu Asn Cys Thr Ala Arg Thr Glu Leu Asn Val Gly
465                 470                 475                 480

Ile Asp Phe Asn Trp Glu Tyr Pro Ser Ser Lys His Gln His Lys Lys
                485                 490                 495

Leu Val Asn Arg Asp Leu Lys Thr Gln Ser Gly Ser Glu Met Lys Lys
            500                 505                 510

Phe Leu Ser Thr Leu Thr Ile Asp Gly Val Thr Arg Ser Asp Gln Gly
        515                 520                 525

Leu Tyr Thr Cys Ala Ala Ser Ser Gly Leu Met Thr Lys Lys Asn Ser
    530                 535                 540

Thr Phe Val Arg Val His Glu
545                 550
```

<210> SEQ ID NO 7
<211> LENGTH: 560
<212> TYPE: PRT
<213> ORGANISM: Artificial Sequence
<220> FEATURE:
<223> OTHER INFORMATION: Synthetic (AV-body 2)

<400> SEQUENCE: 7

```
Met Asp Ser Leu Ala Ser Leu Val Leu Cys Gly Val Ser Leu Leu
1               5                   10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
            35                  40                  45

Trp Arg Pro His Glu Pro Ile Thr Ile Gly Arg Asp Phe Glu Ala Leu
        50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
    210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
    290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Glu Phe Met Gln Ser Lys Val
            340                 345                 350

Leu Leu Ala Val Ala Leu Trp Leu Cys Val Glu Thr Arg Ala Ala Ser
        355                 360                 365
```

-continued

```
Asp Tyr Arg Ser Pro Phe Ile Ala Ser Val Ser Asp Gln His Gly Val
    370             375             380

Val Tyr Ile Thr Glu Asn Lys Asn Lys Thr Val Val Ile Pro Cys Leu
385             390             395             400

Gly Ser Ile Ser Asn Leu Asn Val Ser Leu Cys Ala Arg Tyr Pro Glu
            405             410             415

Lys Arg Phe Val Pro Asp Gly Asn Arg Ile Ser Trp Asp Ser Lys Lys
            420             425             430

Gly Phe Thr Ile Pro Ser Tyr Met Ile Ser Tyr Ala Gly Met Val Phe
        435             440             445

Cys Glu Ala Lys Ile Asn Asp Glu Ser Tyr Gln Ser Ile Met Tyr Ile
450             455             460

Val Val Val Gly Glu Gln Pro Phe Ile Asn Lys Pro Asp Thr Leu
465             470             475             480

Leu Val Asn Arg Lys Asp Ala Met Trp Val Pro Cys Leu Val Ser Ile
            485             490             495

Pro Gly Leu Asn Val Thr Leu Arg Ser Gln Ser Ser Val Leu Trp Pro
        500             505             510

Asp Gly Gln Glu Val Val Trp Asp Asp Arg Arg Gly Met Leu Val Ser
        515             520             525

Thr Pro Leu Leu His Asp Ala Leu Tyr Leu Gln Cys Glu Thr Thr Trp
    530             535             540

Gly Asp Gln Asp Phe Leu Ser Asn Pro Phe Leu Val His Ile Thr Gly
545             550             555             560
```